United States Patent
Njemanze (10) Patent No.: US 7,942,820 B2
(45) Date of Patent: May 17, 2011

(54) METHOD AND SYSTEM FOR EVALUATION OF THE HEMODYNAMIC MODEL IN DEPRESSION FOR DIAGNOSIS AND TREATMENT

(76) Inventor: Philip Chidi Njemanze, Owerri (NG)

(*) Notice: Subject to any disclaimer, the term of this patent is extended or adjusted under 35 U.S.C. 154(b) by 789 days.

(21) Appl. No.: 11/845,085

(22) Filed: Aug. 26, 2007

(65) Prior Publication Data
US 2009/0054774 A1 Feb. 26, 2009

(51) Int. Cl.
A61B 8/00 (2006.01)
(52) U.S. Cl. .......................... 600/441; 600/454
(58) Field of Classification Search .................... 600/441
See application file for complete search history.

(56) References Cited

U.S. PATENT DOCUMENTS
2003/0225335 A1* 12/2003 Njemanze ............ 600/504
2004/0158155 A1* 8/2004 Njemanze ............ 600/454
* cited by examiner Primary Examiner — Tse Chen
Assistant Examiner — Hien Nguyen (57) ABSTRACT

The present invention provides a method for determining the cerebral hemodynamic model for depression, using carotid duplex ultrasound to establish percent stenosis of a right external carotid artery and a left external carotid artery, and transcranial Doppler ultrasound instrument to measure mean flow velocity within the cerebral arteries including the right and left internal carotid arteries, right and left middle cerebral arteries, right and left anterior cerebral arteries, right and left posterior cerebral arteries, and basilar artery. Percent carotid stenosis and mean flow velocity values in cerebral arteries are used to determine the cerebral hemodynamic model associated with depression in men and women, respectively.

20 Claims, 5 Drawing Sheets

METHOD AND SYSTEM FOR EVALUATION OF THE HEMODYNAMIC MODEL IN DEPRESSION FOR DIAGNOSIS AND TREATMENT

CROSS REFERENCE TO RELATED APPLICATION

Not applicable

US PATENT DOCUMENTS

| U.S Pat. No. 6,663,571 | December 2003 | Njemanze PC | 600/504 |
| U.S Pat. No. 6,899,730 | May 2005 | Rivelli, Jr | 623/1.15 |
| U.S Pat. No. 6,936,056 | August 2005 | Nash, et al. | 606/159 |
| U.S Pat. No. 7,150,736 | December 2006 | Barbut et al. | 604/544 |
| U.S Pat. No. 7,226,473 | June 2006 | Brar et al. | 623/1.11 |

STATEMENT REGARDING FEDERALLY SPONSORED RESEARCH OR DEVELOPMENT

Not applicable

REFERENCE TO MICROFICHE APPENDIX

Not Applicable

BACKGROUND OF THE INVENTION

Major depression has been linked to recurrent stroke. It has been established that depression occurs in 10% to 27% of patients who suffer a first or recurrent stroke. In the United States, there are at least 500,000 new ischemic strokes yearly, and about 150,000 stroke survivors would develop post-stroke depression each year.

The risk of developing stroke is four times greater in those with symptoms of depression. The location of brain injury may determine the severity of post-stroke depression. Cerebrovascular changes may lead to depressive disorders. The term 'vascular depression' has been applied to underscore the significance of vascular pathology in the pathogenesis of depression. Depressive disorders showed a male:female ratio of about 1:2.

Carotid artery stenosis is a well known risk factor for stroke. High grade carotid artery stenosis was associated with depressive symptoms in patients with atherosclerosis. It has been observed that, depressive symptoms during early adulthood have been associated with higher levels of carotid intima-media thickening in men, but not in women. Major depression has been linked to decreased cerebrovascular reactivity, which predisposes to increased risk for stroke, in depressed patients. Although it has been known that impaired cerebral perfusion may occur in major depression, the findings have been inconclusive, and measures to relieve cerebral ischemia have not been implemented until now. A wide range of measures for cerebral perfusion augmentation in patients suffering from global or focal cerebral ischemia have been attempted for other indications. The U.S. Pat. No. 7,150,736 to Barbut describes an elongated catheter and a distally mounted expandable balloon to dilate the artery and augment blood flow. Others have used stent deployment at the site of arterial stenosis as described in U.S. Pat. No. 7,226,473 to Brar et al., and U.S. Pat. No. 6,899,730 to Rivelli, Jr. The U.S. Pat. No. 6,936,056 to Nash applies the use of atherectomy catheter to open a lumen of an occluded blood vessel. However, all these measures to augment blood flow have not been applied as a means for treatment of depression because the pathogenesis of depression and associated changes in blood flow to regions of the brain has not been elucidated.

The use of the present invention to provide a model of the cerebral hemodynamics in depression would be of use in a wide range of disease conditions for diagnosis, evaluation of treatment options, effectiveness of surgical measures, and monitoring of progress under certain medications. One object of the present invention is its application to the differential diagnosis for major depression that is of vascular origin. Depression could be a syndrome of many other brain conditions and may be related to vascular pathology. Usually, depression is diagnosed using clinical criteria according to questionnaire items in the diagnostic and statistical manual version 4 (DSM-IV). The use of the present invention to evaluate changes in the cerebral blood flow supply in association with clinical assessment using DSM-IV depression scale would provide the much needed objective diagnostic criteria for depression.

Another object of the present invention is to apply the model for assessment of treatment options. The assessment of the level of ipsilateral cerebral hypoperfusion and contralateral hyperperfusion, would determine to what extent measures need to be taken to relieve the vascular pathology. The choice of life style modification, medication or surgery could be made on the basis of established levels of cerebral blood flow velocity, in the major vessels of the artery of the circle of Willis.

A further object of the invention is the choice of the form of surgery that may be performed. There are a number of options with associated risk levels of surgery that may be used to relieve symptoms of depression, in the presence of carotid artery stenosis. The choice of stent deployment, intravascular atherectomy and endarterectomy, could be made based on the predicted level of blood flow velocity increase expected after the surgery. It has been known that psychological changes occur after open-heart surgery in some patients. A pre-surgery assessment using the model will define the risk of depression and also post-surgery changes could be evaluated and the treatment options assessed.

The present invention was used to postulate that, blood flow shunting through the anterior communicating artery (ACoA) may not be sufficient to equilibrate flow in both anterior cerebral arteries (ACAs) in depressed patients. About 60% of routine autopsy showed anomalous usually multi-channel ACoA. Anomalous ACoA is unable to equilibrate blood flow in both ACAs, creating a hemodynamic condition ipsilateral hypoperfusion and contralateral hyperperfusion. Similarly, the present invention could be applied to diagnosis of atresia, stenosis and other malformations of the ACoA that does not allow adequate blood flow through it.

Furthermore, the present invention could be used alone or in conjunction with magnetic resonance angiography to evaluate the effectiveness of measures such as balloon catheter angioplasty, stent deployment, and arterial grafts for restoration of flow through the ACoA.

Another object of the present invention is its application to the monitoring of patient's progress, while on medication with statins. Generally, statins are used for treatment of carotid plaque disease. The choice of statins in depression is based on their effect on carotid plaque, to improve cerebral perfusion and relieve symptoms of depression.

Yet another object of the present invention is its application to the monitoring of patients progress while on medication with vasodilators, such as pentoxyphylline. In general, vasodilators are used to improve cerebral perfusion. In view of the present invention, vasodilators such as pentoxyphylline, isosorbide dinitrate, and vinpocetine, could be applied in depression; and the present invention provides a means for monitoring their effects.

Another objective of the present invention is to provide a means for monitoring the effects of alternative medicine measures such as herbs, chocolates, acupuncture, light therapy, colored light therapy on cerebral perfusion, and possible effects on depressive symptoms.

A further object of the present invention is its use, for assessment of different lifestyle modification measures, including the use of diet, exercise and work/rest regimen. Assessment of routines that promote better cerebral perfusion and prevent depression would be useful to increase worker productivity.

Another object of the present invention is to assess the effect of posture on cerebral perfusion and depression. Certain postures such as head-down bed rest at −6 degrees have been associated with changes in cerebral perfusion. The latter was used to simulate the cardiovascular effects of microgravity. It may also suggest that, the model could be used to assess astronaut's risk of developing depression in-flight.

Yet another object of the present invention is to use the model, to assess the effects of measures such as lower body negative pressure (LBNP), on cerebral perfusion and the risk of depression. LBNP may be used to simulate the effects of space-flight, and could also be applied to assess the predisposition to development of cerebral hypoperfusion and hence depression. The present invention in conjunction with LBNP could be used to monitor cerebral perfusion in astronauts. Furthermore, the present invention is applicable to astronauts and divers for training assessment, before, during and after execution of mission.

Another object of the present invention is its application for assessment of the effects of hypothermia on cerebral perfusion, and its possible application to depression. Hypothermia is known to affect cerebral perfusion. However, it is not known how hypothermia may change cerebral blood flow and affect depression.

The present invention provides a method for assessment of the effects of synthetic odors and pheromones on cerebral perfusion and hence depression. As have been described in U.S. Pat. No. 6,663,571 to Njemanze P C, odors may affect cerebral mean blood flow velocity. Certain odors could be used to improve blood flow to the brain in depressed patients; the model permits the selection of these odors, to be incorporated into odorants.

SUMMARY OF THE PRESENT INVENTION

The present invention provides a method for determining the cerebral hemodynamic model for depression using carotid duplex ultrasound to establish percent stenosis of the extracranial right and left internal carotid arteries (RICA, LICA), respectively; and transcranial Doppler to measure MFV within the arteries of the circle of Willis including the right and left internal carotid arteries (RICA, LICA), right and left middle cerebral arteries (RMCA, LMCA), right and left anterior cerebral arteries (RACA, LACA), right and left posterior cerebral arteries (RPCA, LPCA), and basilar artery (BA).

The special embodiment of this invention is illustrated in the specification, it includes block and schematic diagrams for the format of the instrumentation, and how the method functions is shown by way of example. The subject refers to a human under testing, by way of example.

The method comprises a carotid duplex ultrasound for establishing the percent stenosis in the extracranial portion of the carotid system; a transcranial Doppler ultrasound for measurement of cerebral mean blood flow velocity (MFV) and computer software for modeling the cerebral hemodynamics. The carotid duplex color flow ultrasound may use high-frequency probe such as 7.5 MHz and the pulsed Doppler wave, to establish the percent stenosis at a given site in the RICA and LICA. The transcranial Doppler instrument with pulsed wave 1 MHz or 2 MHz ultrasound transducer or probe may be used. The transcranial Doppler ultrasound probe is placed on the acoustic window of the temporal bone above the zygomatic arc on both sides of the head, and focused on major cerebral vessels such as RICA, LICA, RMCA, LMCA, RACA, LACA, RPCA, LPCA, and BA. The established MFV pattern is fitted into software, which would be used to simulate the cerebral hemodynamic model, or printed as hardcopy for evaluation.

In contrast to conventional approach, that assumes hypoperfusion in the cerebral arteries as the cause for depression, and does not differentiate the multiple clinical manifestations associated with hypoperfusion, the present invention differentiates gender-related hemodynamic changes that are associated with depression.

Moreover, in contrast to conventional approaches, there is provided in accordance to the teachings of the present invention a male cerebral hemodynamic model and a female cerebral hemodynamic model for depression. Depression has been associated with cerebral hypoperfusion. Cerebral hyperperfusion could be described as when the MFV increased higher than normal limits found in healthy subjects; while cerebral hypoperfusion could be described as MFV lower than normal limits. The male cerebral hemodynamic model provides for hypoperfusion in the RACA, with relative hyperperfusion in the LACA. On the other hand, the female cerebral hemodynamic model provides for LACA hypoperfusion and RACA hyperperfusion.

Thus, it will be appreciated that a cerebral hemodynamic model constructed in accordance with the present invention simulates with accuracy, in less computational time and reduced cost and complexity of implementation, whether in a computer program or hardcopy assessment of results, in conjunction with clinical information.

In addition, a cerebral hemodynamic model for depression constructed in accordance with the present invention can provide a single diagnosis of depression based on multiple inputs of MFV in cerebral arteries.

These and other objects of the present invention may become apparent to those skilled in the art upon reviewing the description of the invention as set forth hereinafter, in view of its drawing.

DETAILED DESCRIPTION OF THE INVENTION

Figure 1:
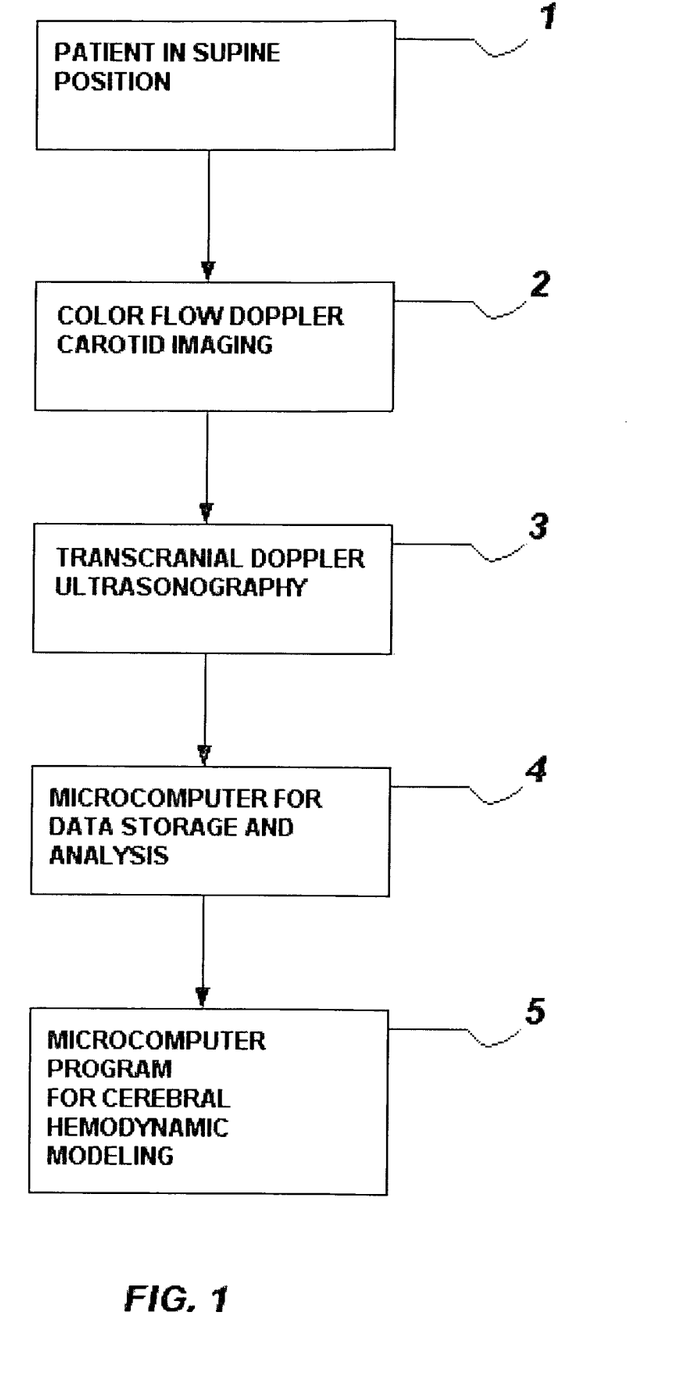
FIG. 1 shows the schematic diagram of the instruments of the present invention.

The block diagram of the present invention is illustrated in FIG. 1. As shown, a subject for investigation referred to here as patient 1 is placed in supine position. Color flow imaging 2 with a 7.5 MHz transducer by way of example, of a device such as Color Flow Mapping, Biosound Esaote, Indianapolis, Ind., is used to scan the carotid arteries. The percent stenosis of the right (% RICA) and left (% LICA) internal carotid arteries is determined based on B-mode and Doppler parameters, respectively. Thereafter, the transcranial Doppler ultrasound sonography 3 such as 2 MHz probe of a Multi-Dop T, manufactured by DWL, Singen Germany, could be used to determine the MFV in all major intracranial vessels including RICA, LICA, RACA, LACA, RMCA, LMCA, RPCA, LPCA and BA, respectively. The acquired data could be documented in hardcopy or stored in a microcomputer 4 for further analysis, and could be interfaced with a program for simulation of cerebral blood flow hemodynamics.

Figure 2:
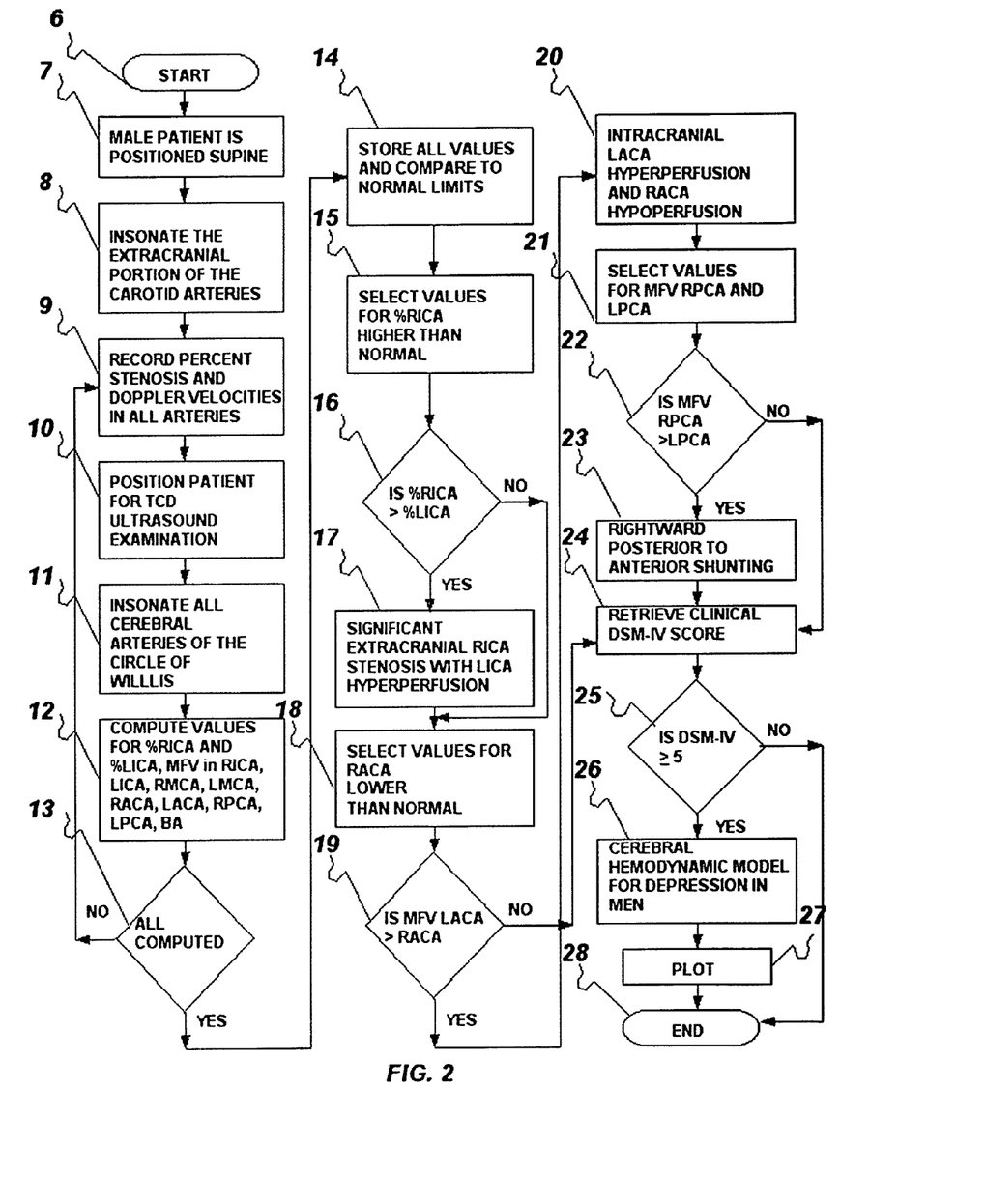
FIG. 2 shows the program flow chart of the present invention for cerebral hemodynamic model in men.

As shown in FIG. 2, at the start 6 of the flow chart, for the procedure in men, the patient is positioned supine on an appropriate examination table 7. The extracranial carotid arteries are examined 8, and the percent stenosis 9 of the internal carotid artery noted, using color flow Doppler velocity criteria and B-mode imaging parameters. Thereafter, the patient is placed in supine position for transcranial Doppler sonography 10. All major cerebral arteries of the circle of Willis are insonated 11, and all values for % RICA, % LICA, MFV in RICA, MFV in LICA, MFV in RMCA, MFV in LMCA, MFV in RPCA, MFV in LPCA, and MFV in BA, are entered in the computer 12. When all values have been computed 13, then the procedure is continued, but if not 13, the preceding steps 9-12 are repeated. All values are then stored and compared with the normal limits set by the investigator 14. Select the value for % RICA that is higher than normal limit 15. When the value is higher than normal limits, compare % RICA and % LICA, if % RICA is greater than % LICA 16, proceed to the next step that implicates extracranial RICA stenosis with hypoperfusion and lack of significant plaque in the LICA with hyperperfusion 17. If not 16, then jump step 17, to select values of RACA, that are lower than normal limits 18. When MFV in the LACA is greater than in the RACA 19, this would implicate RACA hypoperfusion and relative LACA hyperperfusion 20. Then proceed to examine the posterior circulation, by selecting values for RPCA and LPCA at step 21. If the MFV in the RPCA is greater than MFV in the LPCA 22, then a rightward posterior-to-anterior shunting may be present 23. However, if not 22, proceed to use clinical criteria from DSM-IV score to base diagnosis 24. If the DSM-IV score is greater than or equal to five 25, then the determined model of cerebral hemodynamics could be associated with depression in men 26, and should be plotted or simulated with a computer 27 before the program is brought to an end 28. If DSM-IV is lower than five 25, then the patient is not depressed and the program could be brought to an abrupt end 28.

Figure 3:
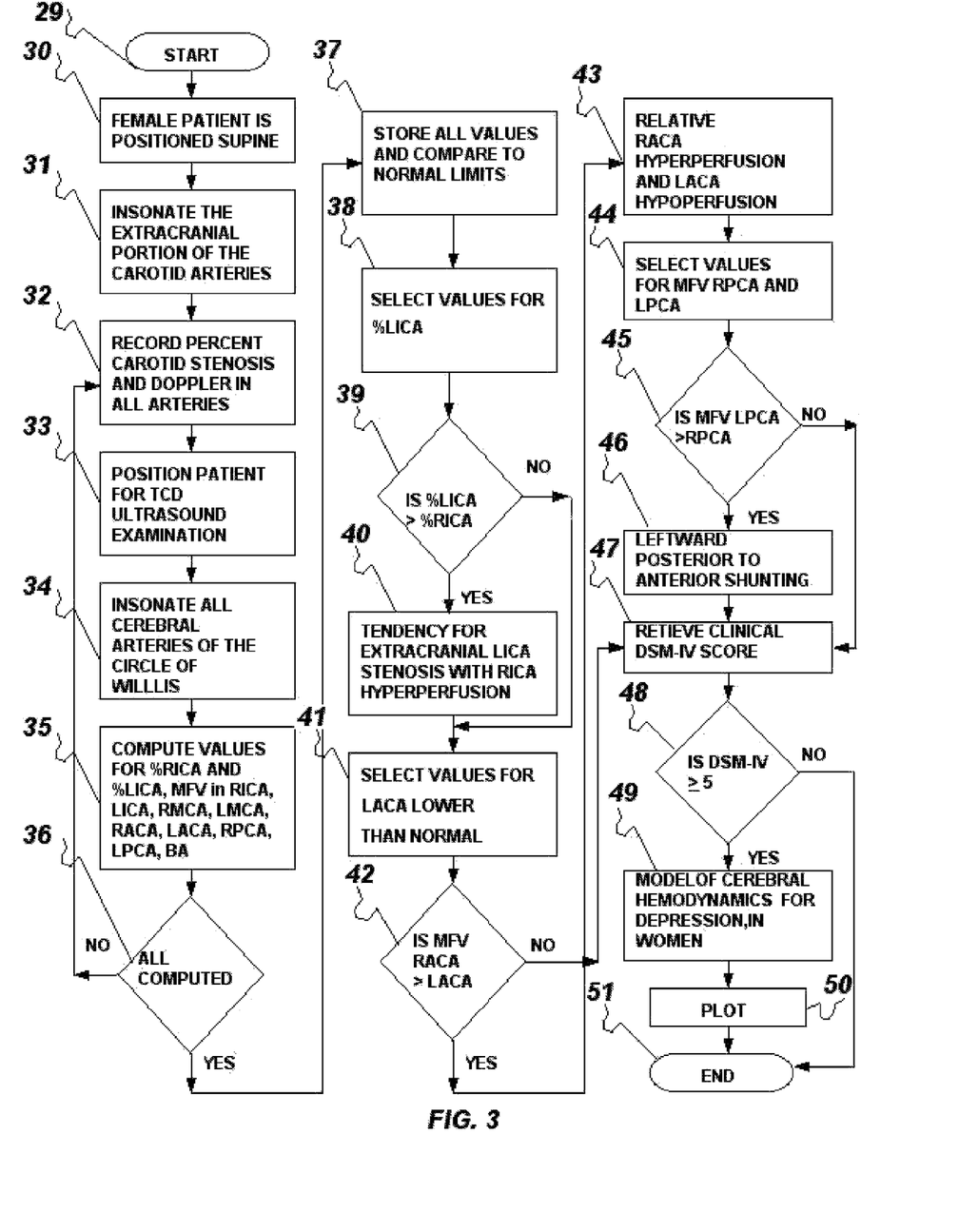
FIG. 3 shows the program flow chart of the present invention for cerebral hemodynamic model in women.

As shown in FIG. 3, at the start 29 of the flow chart, for the procedure in women, the patient is positioned supine on an appropriate examination table 30. The extracranial carotid arteries are examined similar to procedure in men 31, and the percent stenosis 32 of the internal carotid artery noted using color flow Doppler velocity criteria and B-mode imaging. Thereafter, the patient is placed in position for transcranial Doppler sonography 33 similar to the procedure in men. All major cerebral arteries of the circle of Willis are insonated 34, and all values for % RICA, % LICA, MFV in RICA, MFV in LICA, MFV in RMCA, MFV in LMCA, MFV in RPCA, MFV in LPCA, and MFV in BA, are entered in the computer 35. When all values have been computed 36, then the procedure is continued, but if not 36, the preceding steps 32-35 are repeated. All values are then stored and compared with the normal limits set by the investigator 37. Select the value for % LICA 38 and compare to % RICA 39. If % LICA is greater than % RICA 39, proceed to the next step that implicates extracranial LICA stenosis with hypoperfusion and lack of significant plaque in the RICA with hyperperfusion 40. If not 39, then jump to step 41, to select values of LACA, that are lower than normal limits 41. When MFV in the RACA is greater than in the LACA 42, this would implicate RACA hyperperfusion and LACA hypoperfusion 43. Then proceed to examine the posterior circulation, by selecting values for RPCA and LPCA at step 44. If the MFV in the LPCA is greater than MFV in the RPCA 45, then a leftward posterior to anterior shunting may be present 46. However, if not 45, proceed to use clinical criteria from DSM-IV score to base diagnosis 47. If the DSM-IV score is greater than or equal to five 48, then the determined model of cerebral hemodynamics could be associated with depression in women 49, and should be plotted or computer simulated 50 before the program is brought to an end 51. If DSM-IV is lower than five 48, then the patient is not depressed and the program could be brought to an abrupt end 51.

Figure 4:
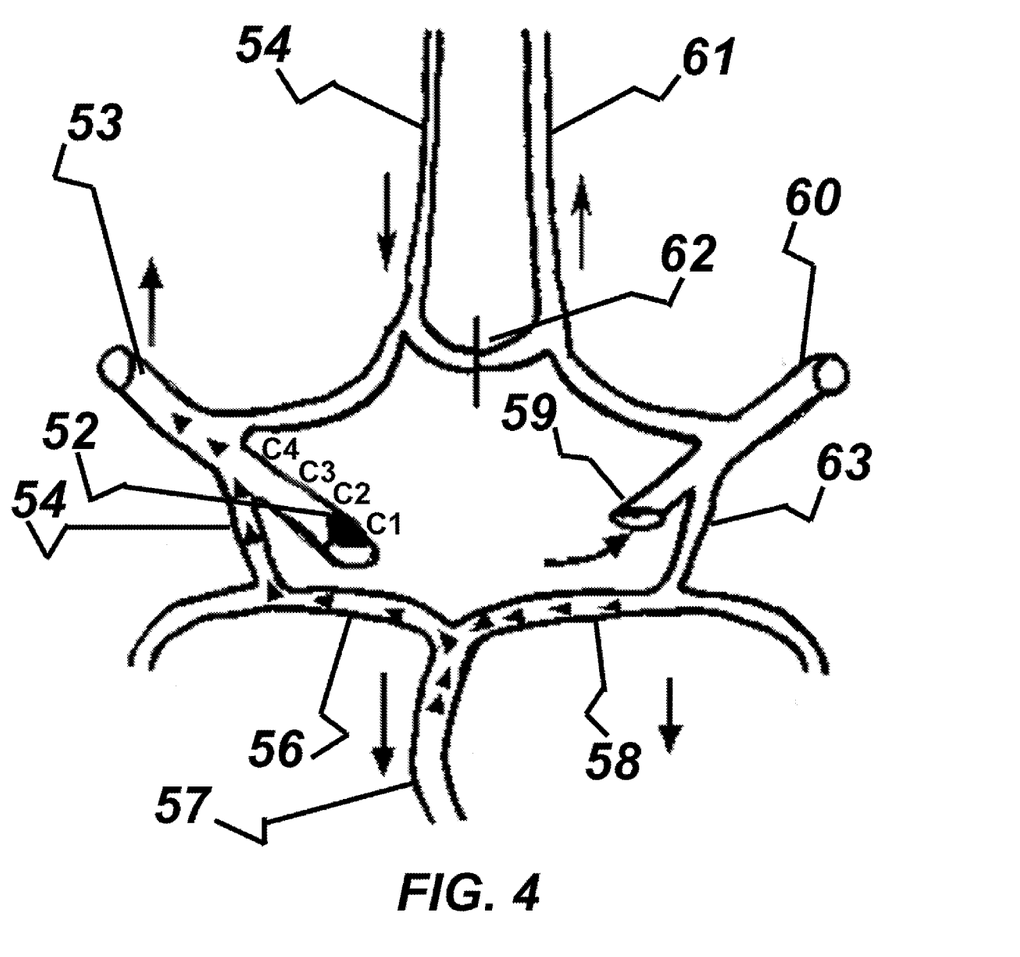
FIG. 4 shows the schematic diagram of the circle of Willis, and representations with arrows, of proposed changes in MFV, associated with the cerebral hemodynamic model for men, established with the present invention.

FIG. 4 shows the schematic diagram of the circle of Willis, and representations with directional arrows, of proposed changes in MFV, associated with the cerebral hemodynamic model for men, established with the present invention. The plaques 52 in the RICA caused a stenotic flow reduction in the post-stenotic segment of the internal carotid artery. The effect on volume flow could be simulated using Hagen-Poiseuille's law. The Hagen-Poiseuille law is the physical law concerning the voluminal laminar stationary flow $\Phi$ of incompressible uniform viscous liquid (so called Newtonian fluid) through a cylindrical tube with constant circular cross-section, experimentally derived by Jean Louis Marie Poiseuille (1797-1869), and defined by:

$$\Phi = \frac{dV}{dt} = v\pi R^2 = \frac{\pi R^4}{8\eta}\left(\frac{-\Delta P}{\Delta x}\right) = \frac{\pi R^4}{8\eta}\frac{|\Delta P|}{L}$$

where V is a volume of the liquid, poured in the time unit t, v the median fluid velocity along the length of the tube, x the direction of flow, R the internal radius of the tube, P the pressure difference between the two ends, η the dynamic fluid viscosity, and L the total length of the tube in the x direction. The RICA 52 branches into the RMCA 53 and RACA 54, its segment could be subdivided into four parts: the C1 or cervical portion; the C2 or petrous portion; the C3 or cavernous portion; and the C4 or supraclinoid portion. The link between extracranial carotid artery disease and depression could be related to diminution of blood supply from the carotid system, to the structures of the mesiobasal limbic system that, comprise the vital neural substrates for affective information processing. The structures of mesiobasal limbic system include: the uncus, amygdaloid body, hippocampus, dendate gyrus, subiculum, fasciolar gyrus and the parahippocampal gyrus. With carotid stenosis present in the C1 region, perfusion pressure would drop progressively, and expected to be minimal at the C4 portion. The C4 portion could be subdivided into three segments based on the origin of its major branches:

the ophthalmic segment extends from the origin of the ophthalmic artery to the origin of the PCoA 55; the communicating segment extends from the origin of the PCoA 55 to the origin of the anterior choroidal artery (AChA); and the choroidal segment extends from the origin of the AChA to the bifurcation of the carotid artery. In the presence of carotid stenosis, the perfusion pressure within the choroidal segment would drop to minimal levels; such that, the perfusion pressure in the perforating branches from the ipsilateral choroidal segment, that pass upward and enter the brain through the anterior perforated substance, would expectedly be very low. Blood flow from the ipsilateral posteromedial and posterolateral choroidal arteries, which are branches of the posterior cerebral artery that forms anastomosis with the terminal end of the AChA, shunts into the AChA. Furthermore, the progressive fall in perfusion pressure creates a flow gradient from the C2, C3 segments to the C4 portion of the ipsilateral carotid artery. This would reduce flow to the RMCA 53 and RACA 54. Furthermore, shunting of blood flow from the ipsilateral RPCoA 55, through the RPCA 56 into the C4 portion, diminishes blood flow in the BA 57 and LPCA 58. The metabolic demand in the RMCA territory that, supplies blood to over 80% of the brain, would require most of the shunted blood flow from the posterior-to-anterior circulation, leaving a diminishing blood supply to the RACA 54, and to the rostral third of the temperomedial region within the AChA territory.

Conversely, on the left side segment of the LICA 59 there is no significant stenosis, and blood to the LMCA 60 and LACA 61 may be at normal levels. Given this asymmetry in RACA 54 and LACA 61 blood flow velocities, a functional ACoA 62, would have blood flow across from the LACA 61 to equilibrate with that in the RACA 54. However, as would be seen in the experiment cited below this is not the case, rather there was a significant asymmetry with MFV in the LACA 61 greater than MFV in the RACA 54. The latter may suggest that there was a non-functional shunting through the ACoA.

Figure 5:
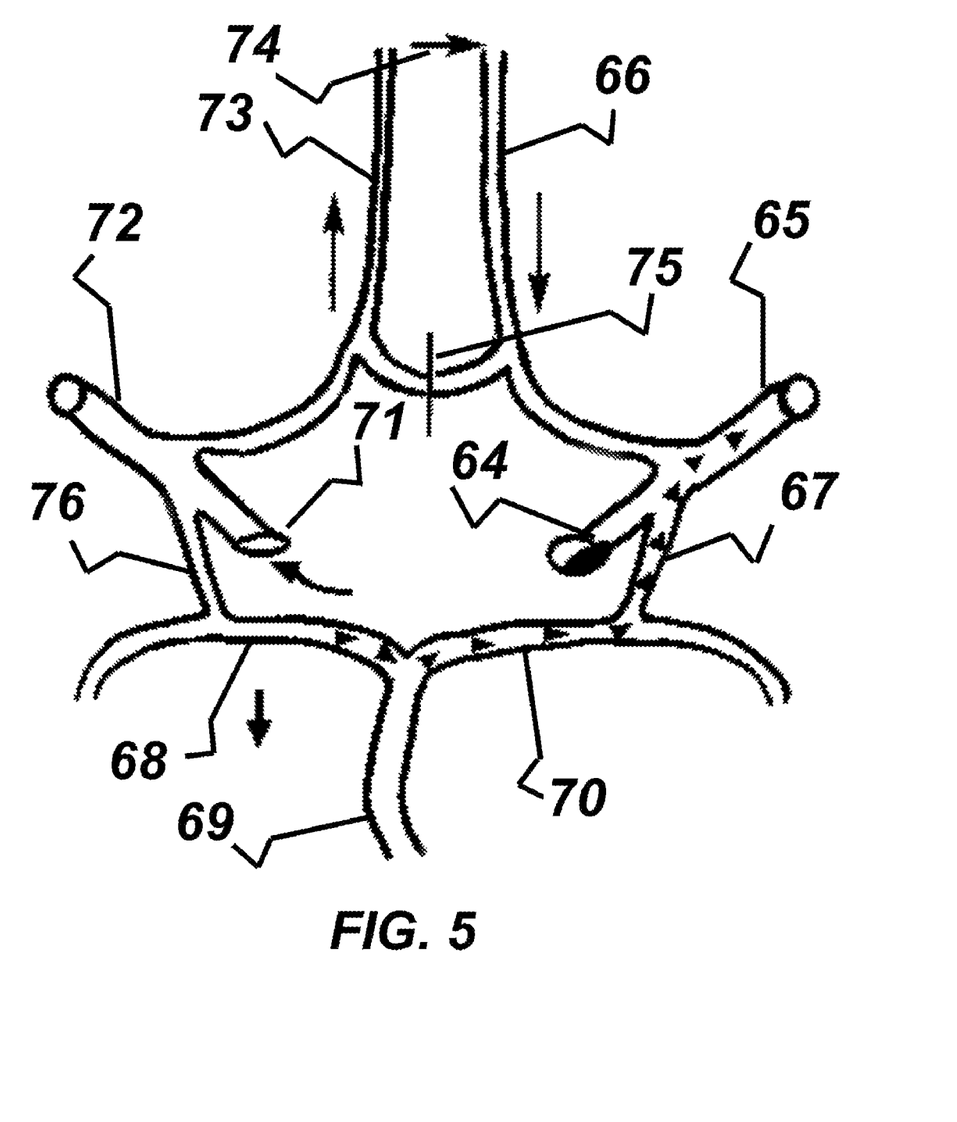
FIG. 5 shows the schematic diagram of the circle of Willis, and representations with arrows, of proposed changes in MFV, associated with the cerebral hemodynamic model for women, established with the present invention.

FIG. 5 shows the schematic diagram of the circle of Willis, and representations with directional arrows, of proposed changes in MFV, associated with the cerebral hemodynamic model for women, established with the present invention. Conversely, in women the threshold for stenosis is lower than in men. There was a tendency for greater stenosis on the left side, creating a hemodynamic condition on the left side as was seen on the right side in men. The LICA stenosis 64 reduces perfusion pressure in the LMCA 65 and LACA 66, creating a condition for posterior-to-anterior shunting through the LPCoA 67, drawing blood flow from the RPCA 68, through the BA 69 and LPCA 70 into the LMCA 65. On the right side, the RICA 71 is free of significant plaque, and normal blood flow goes to the RMCA 72 and RACA 73. The greater perfusion pressure in the RACA 73 may send crossover blood supply 74, through the distal portion to the contralateral LACA region, given that, as in men, shunting through the ACoA 75 may be non-functional. It is known that the distal ACA of one hemisphere sends branches to the contralateral hemisphere in 64% of brains. The crossover blood flow enhances interhemispheric functional connectivity in the depressed patients compared to controls. In long-term depression a 'malfunctional neuroplasticity' may develop and may result in ipsilateral responses for both left and right stimulations. Blood flow in the RPCoA 76 may not reverse direction to prevent RPCA 68 hypoperfusion.

The inventor undertook an experiment in patients with major depression and control subjects without depression to illustrate the use of the present invention for diagnosis of depression. The details of this clinical experiment are described in detail below, by way of example.

Subjects

A total of 100 patients with history of two major cerebrovascular risk factors, including hypertension and carotid artery disease were studied. The group parameters are summarized in table 1.

TABLE 1

Parameters of Basic Anthropometric, Physiologic and Biochemical Variables in all 100 Patients.

| Parameters | Control Men n = 20 | Control Women n = 20 | Depressive Men n = 36 | Depressive Women n = 24 |
|---|---|---|---|---|
| Age (years) | 48.4 ± 10.5 | 48.9 ± 12.1 | 50.8 ± 14.1 | 55.4 ± 15.3 |
| BMI (Kg/m$^2$) | 25.54 ± 3.83 | 28.97 ± 4.21 | 25.99 ± 4.12 | 27.75 ± 4.42 |
| WHR | 0.93 ± 0.05 | 0.87 ± 0.08 | 0.92 ± 0.06 | 0.90 ± 0.05 |
| SBP (mmHg) | 142.7 ± 23 | 145.5 ± 23.3 | 135.6 ± 18.3 | 148.6 ± 25.8 |
| DBP (mmHg) | 92.4 ± 15.5 | 96 ± 17 | 88 ± 12.3 | 90.9 ± 15.6 |
| TCHOL (mg/dL) | 175.8 ± 71.6 | 208.2 ± 76.7 | 198.6 ± 66.2 | 183.7 ± 83.8 |
| LDL (mg/dL) | 79.3 ± 26.4 | 118.9 ± 52.4 | 101.1 ± 51.9 | 97.5 ± 82.5 |
| HDL (mg/dL) | 66.2 ± 51.6 | 67.2 ± 46.8 | 67.8 ± 56.6 | 62.2 ± 39.6 |
| TGL (mg/dL) | 151.5 ± 76.3 | 111.6 ± 37.9 | 129.2 ± 84.1 | 131.7 ± 80.7 |
| VLDL (mg/dL) | 30.3 ± 15.2 | 22.2 ± 7.5 | 25.8 ± 16.8 | 28 ± 16.9 |
| % RICA | 51.8 ± 21.9 | 58.85 ± 18.7 | 74.2 ± 12.6 | 66 ± 18 |
| % LICA | 47.4 ± 20.6 | 61.6 ± 14.5 | 69 ± 14.2 | 67.7 ± 21.2 |

The study group comprised 60 consecutive patients (36 men and 24 women), who in addition to cerebrovascular risks had clinical depression. The control group included 40 patients who had cerebrovascular risk factors without clinical depression. There was no difference in age between the groups (p<0.05). All subjects were right handed, with the preferred hand determined using a standardized questionnaire. Clinical history and standard clinical examination included measurement of systolic (SBP) and diastolic (DBP) blood pressures and pulse. All subjects underwent a full neurological examination, including the National Institutes of Health Neurologic Stroke Scale (NIHSS). Stroke was defined according to the WHO criteria. Brain scans were obtained as indicated. No subject had a history of psychiatric disorders other than depression, and none used recreational drugs. All subjects were screened for depression with the PHQ-9, a 9 item scale that assesses the 9 symptoms according to the Diagnostic and Statistical Manual of Mental Disorders (DSM-IV) criteria, for frequency of occurrence during the preceding 2 weeks. The first two items of the DSM-IV criteria: depressed mood and anhedonia had to be present along with other items so that, a score of 5 to 9 out of 9 symptoms, have been present at least more than half the days of the past 2 weeks, for the subject to be considered depressed. All items were translated into local languages, if subject could not comprehend English language meaning of the questions. Only baseline scores based on the DSM-IV 9-point scale (presence or absence of each item) were used for further analyses, rather than the frequency scores on PHQ-9. Blood samples were collected for hematological and biochemical analysis. Lipid profile (LIPIDS) including: total cholesterol (TCHOL), low density lipoproteins (LDL), high density lipoproteins (HDL), triglycerides (TGL) and very low density lipoproteins (VLDL), were determined using the enzymatic technique. Anthropometric variables were used to calculate the body mass index (BMI), as weight divided by height squared (kg/m2); waist-to-hip ratio (WHR) was calculated as waist (cm) divided by hip (cm). Subjects were non-smokers. No subject used caffeine within 24 hours preceding the study. Drugs, other than those required for blood pressure control, that could alter cerebrovascular reactivity, were all suspended, for at least five half-lives of the drug before the study. No subject was prior to evaluation, on antidepressants or other psychoactive drugs. The transcranial Doppler (TCD) ultrasonography was performed using a 2 MHz pulsed Doppler transducer of a Multi-Dop T (DWL Singen Germany), to measure MFV in all major cerebral arteries (RMCA, LMCA, RICA, LICA, RACA, LACA, RPCA, LPCA and BA) of the circle of Willis. The sonic windows on the temporal bones on both sides of the head were used. Color-flow Doppler and B-mode ultrasound (Color Flow Mapping System, Biosound, Esaote, Indianapolis Ind.) of the right and left carotid arteries, were used to determine % RICA and % LICA, according to the European Carotid Surgery Trial (ECST) measurement protocol. All subjects gave informed consent according to guidelines of the Institutional Review Board and the Declaration of Helsinki.

Statistical Analysis

All data were stored in a microcomputer and were later analyzed using a statistical software package (Statistica, Stat-Soft, OH). Basic descriptive statistics and analysis of variance (ANOVA) were performed to examine group differences. A multiple regression model was used to analyze MFV values to determine the beta, partial and semi-partial correlation coefficients. The level of significance was set at $p<0.05$.

Results

To examine the effects of the different risk factors (BMI, WHR, SBP, DBP, LIPIDS, % RICA, % LICA, NIHSS) on depression, an ANOVA was performed with a 2×2 design: two levels of GENDER (men and women), two levels of DEPRESSION status (depression and control groups). Each risk factor was analyzed as the dependent variable, respectively. Except for % RICA, % LICA and NIHSS, other factors had no main effect on DEPRESSION, p=NS. For % RICA, there was no main effect of GENDER, p=NS. There was a main effect of DEPRESSION, $F(1,96)=17.2$, MSE=5161.1, $p<0.0001$. Depression was associated with greater % RICA (70.1%) than in controls (55.3%), Schaeffe post hoc, $p<0.0001$. There was a GENDER×DEPRESSION interaction, $F(1,96)=4.59$, MSE=1376.5, $p<0.05$. The observed association of depression with % RICA was in men, with % RICA in the depression group (74.2%) greater than in the control group (51.8%), Schaeffe post hoc, $p<0.001$; however, in women, the % RICA in the depression group (66%), showed only a tendency to be greater than that in the control group (59%), p=NS. For % LICA, there was no main effect of GENDER, p=NS. There was a main effect of DEPRESSION, $F(1,96)=14.8$, MSE=4554.5, $p<0.001$. Depression was associated with greater % LICA (68.3%) than in the control group (54.5%), Schaeffe post hoc, $p<0.001$. There was a GENDER×DEPRESSION interaction, $F(1,96)=4.6$, MSE=1411.3, $p<0.05$. Similarly, the observed association of depression with % LICA was in men, with % LICA in the depression group (69%) greater than in the control group (47.4%), Schaeffe post hoc, $p<0.001$; but in women, the % LICA in the depression group (67.7%) showed only a tendency to be greater than in the control group (61.6%), Schaeffe post hoc, p=NS. In other words, for both % RICA and % LICA, women had a lower threshold of percent stenosis for depression than men. For NIHSS score, there was no main effect of GENDER, p=NS. There was a main effect of DEPRESSION, $F(1,96)=30.3$, MSE=953.1, $p<0.0001$. The mean NIHSS score was 6.4 in the depression group and zero (0) in the control group. The severity of depression did not differ between the 29/60 (or 48.3%) patients who had stroke (mean DSM-IV score=7.5±1), and the 31/60 (or 51.7%) patients who had no stroke (mean DSM-IV score=7.6±1).

To examine the effect of brain regional blood flow supply, as indexed by MFV measurements in the major cerebral arteries (RMCA, LMCA, RICA, LICA, RACA, LACA, RPCA, LPCA, and BA, respectively) on depression, an ANOVA was performed with a 2×2 design: two levels of GENDER (men and women), and two levels of DEPRESSION (depression and control groups). The MFV in each artery was analyzed as the dependent variable, respectively. For RMCA, LMCA, RICA, LICA, LPCA and BA, respectively, there was no main effect of DEPRESSION, p=NS, and there were no interactions, p=NS. However, for the RACA, there was no main effect of GENDER, p=NS. There was a main effect of DEPRESSION $F(1,96)=5$, MSE=872, $p<0.05$. The patients in the depression group had lower levels of MFV in the RACA (42.3 cm/s) compared to those of the control group (48.4 cm/s), Schaeffe post hoc, $p<0.05$. In the LACA, there was no main effect of GENDER, p=NS. There was no main effect of DEPRESSION, p=NS. There was a tendency for a GENDER×DEPRESSION interaction, $F(1,96)=3.4$, MSE=487.5, p=0.06. For LACA, women of the depression group (38±12 cm/s), had lower MFV than those of the control group (47±14 cm/s), $F(1,42)=4.97$; MSE=838.4, $p<0.05$. However, in the LACA, men of depression group (44±11 cm/s) had the same MFV as those of the control group (44±10 cm/s). For RPCA, there was no main effect of GENDER, p=NS. There was a main effect of DEPRESSION, $F(1,96)=4.3$, MSE=302, $p<0.05$. There was a GENDER×DEPRESSION interaction, $F(1,96)=6.1$, MSE=433, $p<0.05$. Women in the depression group had lower RPCA MFV (29 cm/s) than women of control group (37 cm/s), Schaeffe post hoc, $p<0.05$.

To determine the relative contribution of percent stenosis, on each side of the extracranial carotid system to DSM-IV severity score, a multiple regression analysis was performed with DSM-IV score as the dependent variable, and the % RICA and % LICA as independent variables. In men of depression group, DSM-IV score correlated negatively with % LICA (beta=−0.353, partial=−0.354 and semi partial=−0.346, $p<0.05$); but not with % RICA, p=NS. On the other hand, in women of depression group, DSM-IV score correlated negatively with % RICA (beta=−0.464, partial=−0.425 and semi-partial=−0.418, $p<0.05$); but not with % LICA, p=NS. In other words, there was a gender related inverse correlation of DSM-IV severity score with contralateral carotid intima media thickness.

To determine the relative contribution of MFV in each major intracranial artery to DSM-IV severity score, a multiple regression analysis was performed with DSM-IV score as the dependent variable and the MFV in the arteries (RMCA, LMCA, RICA, LICA, RACA, LACA, RPCA, LPCA and BA) as the independent variables. In men of depression group, the DSM-IV score correlated positively with MFV in the RMCA (beta=0.596, partial=0.41 and semi-partial=0.3, p<0.05); and positively with MFV in the LICA (beta=0.73, partial=0.5 and semi-partial=0.4, p<0.01); but negatively with MFV in the RACA (beta=−0.45, partial=−0.38 and semi partial=−0.27, p<0.05); negatively with MFV in the BA (beta=−0.357, partial=−0.377 and semi-partial=−0.274, p<0.05); and a tendency toward negative correlation with MFV in the LPCA (beta=−0.357, partial=−0.356 and semi-partial=−0.257, p=0.06). In women of depression group, DSM-IV score showed only a tendency towards positive correlation with MFV in the RACA (beta=0.87, partial=0.46 and semi-partial=0.44, p=0.06).

We examined whether the level of ipsilateral hypoperfusion in the ACA region, was related to the level of contralateral hyperperfusion, that is, if there was interhemispheric connectivity of blood flow supply to the contralateral distal ACA territories that contributed to severity of depression. The relationship between MFV in the RACA, MFV in the LACA and DSM-IV score was examined using correlation/regression analysis with linear smoothing. The equation DSM-IV score z=6.58+0.002*x(RACA MFV)+0.019*y(LACA MFV), described the relationship between DSM-IV score and MFV in the RACA and LACA. The slope of relative increase in MFV in the LACA (y=0.019) was ten-fold the slope of the RACA (slope x=0.002), suggesting that hypoperfusion in the RACA was independent in its effect on depression severity, from the effect of the tendency toward hyperperfusion in the LACA. In women of depression group, the equation DSM-IV score z=7.3+0.037*x(RACA MFV)+−0.034*y(LACA MFV) described the relationship between DSM-IV score and MFV in the RACA and LACA. Note that, the RACA positively correlated with DSM-IV score, slope x=0.037, to the same measure as the LACA negatively correlated with DSM-IV score, slope y=−0.034, which may suggest that both processes of RACA hyperperfusion and LACA hypoperfusion could be inter-dependent in their contribution to severity of depression in women. In other words, in women, but not men, it could be presumed that there is interhemispheric connectivity of blood flow supply in both distal ACA territories, such that the loss of ipsilateral perfusion in the left hemisphere was countered by a similar level of contralateral hyperperfusion in the right through crossover collaterals, that contributed to depression severity. The intercept values of 6.58 (for men of depression group) and 7.32 (for women of depression group) may suggest that, at least mild to moderate depression was accounted for, by extracranial circulatory changes.

In summary, the proposed model for men suggests that, in the absence of significant LICA stenosis, an increased MFV in the ipsilateral LICA maintains normal levels of MFV in the LACA and LMCA. The stenotic plaque in the RICA reduces MFV in the RACA. Conversely, the MFV in the RMCA would show a compensatory tendency to increase, due to shunting of blood supply from the posterior circulation (BA and LPCA) through the ipsilateral anastomosis, and right posterior communicating artery (RPCoA) from the RPCA, BA and LPCA. The result is that, both BA and LPCA develop hypoperfusion. The latter, shunting to the right carotid system in men, could be described as a right-ward model. In women, the proposed model of cerebral hemodynamics in depression suggests that, in the absence of significant stenotic plaque in the RICA, a normal MFV in the RICA would maintain normal levels of MFV in the RMCA. However, MFV in the RACA was raised, causing RACA hyperperfusion. Conversely, even moderate levels of stenotic plaque in the LICA, causes a LACA hypoperfusion. The MFV in the LMCA would show a compensatory increase, due to posterior-to-anterior shunting of blood supply through the left posterior communicating artery (LPCoA), from the LPCA and RPCA, and also from the ipsilateral anastomosis. The result is that, the RPCA territory is hypoperfused. The latter shunting system in women was described as a left-ward model. These models account for changes within the major arteries of the circle of Willis in depression.

Even though a preferred embodiment of the present invention is described above, it is contemplated that the numerous modifications may be made thereto for particular applications without departing from the essence and scope of the present invention. The embodiment described could be considered only as illustrative of the present invention and that the scope thereof should not be limited thereto but be determined by reference to the claims hereinafter provided.

I claim:

1. A non-invasive method to determine the cerebral hemodynamics in a human subject with depression using a plurality of ultrasound devices comprising, steps of:
   (a) obtaining a subject's percent carotid stenosis in a right external carotid artery and a left external carotid artery using B-mode and Doppler measurements;
   (b) obtaining mean blood flow velocity for the left and right side of a subject for all major cerebral arteries including internal carotid arteries, middle cerebral arteries, anterior cerebral arteries and posterior cerebral arteries;
   (c) comparing the percent carotid stenosis in both right and left to normal limits;
   (d) determining if the percent carotid stenosis of one side is greater than the other;
   (e) determining if mean blood flow velocity in the right or left anterior cerebral artery is lower than normal limits;
   (f) determining if the mean flow velocity of one side of the anterior cerebral artery is greater than the other;
   (g) determining if there was a right or left anterior cerebral artery hyperperfusion;
   (h) determining if there was a right or left anterior cerebral artery hypoperfusion;
   (i) determining if mean blood flow velocity in the right or left posterior cerebral artery are lower than normal limits;
   (j) determining if mean blood flow velocity of one side of the posterior cerebral artery is greater than the other;
   (k) determining if there was a right or left posterior cerebral artery hypoperfusion;
   (l) determining a DSM-IV score using the standard questionnaire;
   (m) determining if a DSM-IV score was greater than or equal to five; and
   (n) determining if a cerebral hemodynamic model is associated with depression based on the determination of steps (d) through (m).

2. A method as in claim 1 wherein color flow Doppler and B-mode ultrasound devices are used to acquire blood flow velocities and calculate percent carotid stenosis.

3. A method as in claim 2 wherein a transcranial Doppler ultrasound device is used to measure mean cerebral blood flow velocity.

4. A method as in claim 3 wherein the plurality of ultrasound devices are operatively connected to a microcomputer that simulates the cerebral hemodynamic model.

5. A method as in claim 4 wherein percent carotid stenosis in both right and left carotid arteries are used to determine a cerebral hemodynamic model.

6. A method as in claim 5 wherein values of the mean flow velocity in cerebral arteries are used to determine a cerebral hemodynamic model.

7. A non-invasive method to determine the cerebral hemodynamic model in a male subject with depression using a plurality of ultrasound devices comprising, steps of:
  (a) obtaining a subject's percent carotid stenosis in a right external carotid artery and a left external carotid artery using B-mode and Doppler measurements;
  (b) obtaining mean blood flow velocity for the left and right side of a subject for all major cerebral arteries including internal carotid arteries, middle cerebral arteries, anterior cerebral arteries and posterior cerebral arteries;
  (c) comparing the percent carotid stenosis in both right and left to normal limits;
  (d) determining if the percent carotid stenosis of the right is greater than the left;
  (e) determining if mean blood flow velocity in the right anterior cerebral artery is lower than normal limits;
  (f) determining if the mean flow velocity of the left anterior cerebral artery is greater than the right;
  (g) determining if there was a right anterior cerebral artery hypoperfusion;
  (h) determining if there was a left anterior cerebral artery hyperperfusion;
  (i) determining if mean blood flow velocity in the left posterior cerebral artery is lower than normal limits;
  (j) determining if mean blood flow velocity of the right posterior cerebral artery is greater than the left;
  (k) determining if there was a left posterior cerebral artery hypoperfusion;
  (l) determining a DSM-IV score using the standard questionnaire;
  (m) determining if a DSM-IV score was greater than or equal to five; and
  (n) determining if a cerebral hemodynamic model is associated with depression in men based on the determination of steps (d) through (m).

8. A method as in claim 7 wherein color flow Doppler and B-mode ultrasound devices are used to acquire blood flow velocities and calculate percent carotid stenosis.

9. A method as in of claim 8 wherein a transcranial Doppler ultrasound device is used to measure mean cerebral blood flow velocity.

10. A method as in claim 9 wherein the plurality of ultrasound devices are operatively connected to a microcomputer that simulates the cerebral hemodynamic model.

11. A method as in claim 10 wherein percent carotid stenosis in both right and left carotid arteries are used to determine a cerebral hemodynamic model in men.

12. A method as in claim 11 wherein values of the mean flow velocity in cerebral arteries are used to determine a cerebral hemodynamic model in men.

13. A method as in claim 12 wherein a male cerebral hemodynamic model is used for differential diagnosis of depression in men.

14. A non-invasive method to determine the cerebral hemodynamic model in a female subject with depression using a plurality of ultrasound devices comprising, steps of:
  (a) obtaining a subject's percent carotid stenosis in a right external carotid artery and a left external carotid artery using B-mode and Doppler measurements;
  (b) obtaining mean blood flow velocity for the left and right side of a subject for all major cerebral arteries including internal carotid arteries, middle cerebral arteries, anterior cerebral arteries and posterior cerebral arteries;
  (c) comparing the percent carotid stenosis in both right and left to normal limits;
  (d) determining if the percent carotid stenosis of the left is greater than the right;
  (e) determining if mean blood flow velocity in the left anterior cerebral artery is lower than normal limits;
  (f) determining if the mean flow velocity of the right anterior cerebral artery is greater than the left;
  (g) determining if there is a right anterior cerebral artery hyperperfusion;
  (h) determining if there is a left anterior cerebral artery hypoperfusion;
  (i) determining if mean blood flow velocity in the right posterior cerebral artery is lower than normal limits;
  (j) determining if mean blood flow velocity of the left posterior cerebral artery is greater than the right;
  (k) determining if there was a right posterior cerebral artery hypoperfusion;
  (l) determining a DSM-IV score using the standard questionnaire;
  (m) determining if a DSM-IV score was greater than or equal to five; and
  (n) determining if a cerebral hemodynamic model was associated with depression in women based on the determination of steps (d) through (m).

15. A method as in claim 14 wherein color flow Doppler and B-mode ultrasound devices are used to acquire blood flow velocities and calculate percent carotid stenosis.

16. A method as in claim 15 wherein a transcranial Doppler ultrasound device is used to measure mean cerebral blood flow velocity.

17. A method as in claim 16 wherein the plurality of ultrasound devices are operatively connected to a microcomputer that simulates the cerebral hemodynamic model.

18. A method as in claim 17 wherein percent carotid stenosis in both right and left carotid arteries are used to determine the cerebral hemodynamic model in women.

19. A method as in claim 18 wherein values of the mean flow velocity are used to determine the cerebral hemodynamic model in women.

20. A method as in claim 19 wherein a female cerebral hemodynamic model is used for differential diagnosis of depression in women.

* * * * *